United States Patent [19]
Yoon

[11] Patent Number: 5,437,680
[45] Date of Patent: Aug. 1, 1995

[54] SUTURING METHOD, APPARATUS AND SYSTEM FOR USE IN ENDOSCOPIC PROCEDURES

[76] Inventor: InBae Yoon, 2101 Highland Ridge Dr., Phoenix, Md. 21131

[21] Appl. No.: 2,479

[22] Filed: Jan. 6, 1993

Related U.S. Application Data

[60] Continuation-in-part of Ser. No. 719,281, Jun. 19, 1991, Pat. No. 5,366,459, which is a division of Ser. No. 450,301, Dec. 15, 1989, Pat. No. 5,100,418, which is a continuation-in-part of Ser. No. 49,504, May 14, 1987, abandoned.

[51] Int. Cl.$^6$ .............................. A61B 17/04
[52] U.S. Cl. ..................... 606/139; 606/143; 606/144; 606/145; 606/224; 606/232; 606/223
[58] Field of Search ..................... 606/142–148, 606/228–232, 224, 220, 139, 151; 24/16, 30.5 P

[56] References Cited

U.S. PATENT DOCUMENTS

| | | |
|---|---|---|
| 312,408 | 2/1885 | Wackerhagen . |
| 454,327 | 6/1891 | Brown . |
| 818,152 | 4/1906 | Edwards . |
| 1,321,011 | 11/1919 | Cottes . |
| 2,336,689 | 12/1943 | Karle . |
| 3,123,077 | 3/1964 | Alcamo ............................ 606/228 |
| 3,570,497 | 3/1971 | Lemole ............................ 24/16 PB |
| 3,775,825 | 12/1973 | Wood et al. ..................... 606/143 |
| 3,910,281 | 10/1975 | Kletschka et al. ............... 606/252 |
| 4,235,238 | 11/1980 | Ogiu et al. ....................... 606/145 |
| 4,440,171 | 4/1984 | Nomoto et al. ................... 606/224 |
| 4,527,564 | 7/1985 | Equchi et al. . |
| 4,548,202 | 10/1985 | Duncan ............................. 606/220 |
| 4,592,355 | 6/1986 | Antebi . |
| 4,730,615 | 3/1988 | Sutherland et al. .............. 24/30.5 P |
| 4,932,962 | 6/1990 | Yoon et al. ....................... 606/224 |
| 4,935,027 | 6/1990 | Yoon ................................. 606/146 |
| 4,935,028 | 6/1990 | Drews .............................. 606/220 |
| 4,950,285 | 8/1990 | Wilk ................................. 606/232 |
| 4,955,913 | 9/1990 | Robinson ......................... 606/228 |
| 4,966,143 | 10/1990 | Meinershagen . |
| 4,981,149 | 1/1991 | Yoon et al. ....................... 128/898 |
| 4,990,153 | 2/1991 | Richards .......................... 606/148 |
| 5,015,250 | 5/1991 | Foster .............................. 614/147 |
| 5,037,433 | 8/1991 | Wilk et al. ....................... 606/139 |
| 5,053,047 | 10/1991 | Yoon ................................. 606/223 |
| 5,059,201 | 10/1991 | Asnis ............................... 606/144 |
| 5,074,874 | 12/1991 | Yoon et al. ....................... 606/224 |
| 5,078,731 | 1/1992 | Hayhurst .......................... 606/232 |
| 5,084,057 | 1/1992 | Green et al. ..................... 606/142 |
| 5,084,058 | 1/1992 | Li ..................................... 606/148 |
| 5,087,263 | 2/1992 | Li ..................................... 606/148 |
| 5,089,012 | 2/1992 | Prou ................................. 606/224 |
| 5,100,415 | 3/1992 | Hayhurst .......................... 606/139 |
| 5,100,418 | 3/1992 | Yoon ................................. 606/139 |
| 5,100,421 | 3/1992 | Christoudias .................... 606/147 |
| 5,123,913 | 6/1992 | Wilk ................................. 606/232 |
| 5,144,961 | 9/1992 | Chen ................................ 128/898 |
| 5,147,373 | 9/1992 | Ferzli ............................... 606/149 |
| 5,152,769 | 10/1992 | Baber ............................... 606/143 |
| 5,163,946 | 11/1992 | Li ..................................... 606/148 |
| 5,171,250 | 12/1992 | Yoon ................................. 606/142 |
| 5,171,251 | 12/1992 | Bregen et al. .................... 606/151 |
| 5,222,977 | 6/1993 | Esser . |
| 5,224,948 | 7/1993 | Abe et al. . |

FOREIGN PATENT DOCUMENTS

| | | |
|---|---|---|
| 0477020 | 9/1991 | European Pat. Off. . |
| 2651113 | 8/1989 | France . |

*Primary Examiner*—Gary Jackson

[57] ABSTRACT

A method, system and apparatus for suturing tissue in an anatomical cavity during an endoscopic procedure includes a suturing instrument extending through a portal in the anatomical cavity wall for manipulating a needle to penetrate the tissue to form a looped portion of a length of suture material at an exit point in the tissue and to back the needle out of the tissue, and an anchor applier instrument extending through another portal in the anatomical cavity wall for positioning an anchor in engagement with the looped portion of the suture material to allow the suture material to be tensioned and secured to adjustably approximate the tissue.

41 Claims, 11 Drawing Sheets

SUTURING METHOD, APPARATUS AND SYSTEM FOR USE IN ENDOSCOPIC PROCEDURES

REFERENCE TO RELATED APPLICATION

This application is a continuation-in-part of pending application Ser. No. 719,281, filed Jun. 25, 1991, now U.S. Pat. No. 5,366,459, which is a divisional application of Ser. No. 450,301, filed Dec. 15, 1989, now U.S. Pat. No. 5,100,418, which is a continuation-in-part of abandoned application Ser. No. 49,504, filed May 14, 1987, the disclosures of all of said prior applications being incorporated herein by reference.

BACKGROUND OF THE INVENTION

1. Field of the Invention

The present invention pertains to suturing of bodily tissue and, more particularly, to methods, apparatus and systems for suturing tissue during endoscopic procedures.

2. Discussion of the Prior Art

Suturing of bodily tissue is a time consuming part of most surgical procedures including both open surgery and endoscopic or closed surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. In microsurgery, suturing is necessarily time consuming due to the small size of the suture needle and the suture material and the concomitant difficult manipulation required to pass the suture needle through the tissue and to tie a knot in the suture material. With respect to endoscopic surgery, suturing and tying knots represents an even more time consuming procedure due to the difficult maneuvers required. Accordingly, while endoscopic surgery would be preferred for most procedures, the advantages are often outweighed by the disadvantages caused by the length of time required to complete the endoscopic surgical procedure, which time is greatly extended due to the time required for suturing.

There have been many attempts to provide devices to take the place of conventional suturing with a suture needle and a length of suture material; however, such prior art devices have essentially been staples, clips or clamps not allowing any adjustment of tension by the surgeon. French Patent No. 2,651,113 to Alain and U.S. Pat. Nos. 3,123,077 to Alcamo, 3,570,497 to Lemole, 4,548,202 to Duncan, 4,592,355 to Antebi, 4,730,615 to Sutherland et al, 4,935,028 to Drews, 4,950,285 to Wilk, 4,955,913 to Robinson and 5,123,913 to Wilk are representative of prior art devices for use during open surgery to adjustably hold tissue together similar to suturing and tying but fail to provide the same feel and tension control as knotting a length of suture material. U.S. Pat. No. 3,910,281 to Kletschka et al is representative of suture anchors for facilitating tying.

Endoscopic surgery is preferred over open surgery due to the greatly reduced trauma and wound healing time for the patient and due to concomitant cost savings associated with shorter hospital stays and performing surgery without general anesthesia and in non-hospital or out-patient surgery sites. Accordingly, there has been much effort spent to develop techniques for facilitating the suturing normally performed by use of a suture needle and a length of suture material. Alternative techniques proposed have included electrical coagulation, mechanical devices such as clips, clamps and staples, and lasers; however, no well accepted alternative has yet been found in that suturing and tying are essential and vital parts of most surgical procedures. That is, to date the proposed alternatives have had disadvantages, including increased risk to the patient, while not providing the surgeon with the advantages of suturing and tying and not being useful in a wide range of procedures to allow expansion of the areas in which endoscopic surgery can be effectively performed. Thus, there is a great need for suturing techniques useful in endoscopic surgery to permit surgeons to suture with controlled tension and approximation of tissue similar to that obtained by conventional knot tying.

U.S. Pat. No. 3,775,825 to Wood et al discloses apparatus and method for suturing wherein clips are secured on the free ends of a suture filament; however, the apparatus and method are not practical for endoscopic procedures.

U.S. Pat. Nos. 5,078,731 to Hayhurst and 5,171,251 to Bregen et al are representative of clips for clamping suture material to eliminate knotting during endoscopic procedures. European Patent Publication No. 0,477,020A to Chen et al and U.S. Pat. Nos. 5,015,250 to Foster, 5,037,433 to Wilk et al, 5,059,201 to Asnis, 5,084,058 to Li, 5,087,263 to Li, 5,100,415 to Hayhurst, 5,100,421 to Christoudias, 5,144,961 to Chen, 5,147,373 to Ferzli, 5,152,769 to Baber and 5,163,946 to Li are representative of needle holders and apparatus for suturing, knotting or ligating during endoscopic procedures which, however, have the disadvantages of requiring complex instruments, of requiring special suture devices, of being difficult to manipulate and/or of not sufficiently reducing the time required for suturing.

U.S. Pat. Nos. 4,932,962, 4,981,149 and 5,074,874 to Yoon et al and U.S. Pat. Nos. 4,935,027, 5,053,047 and 5,100,418 to Yoon disclose methods and apparatus particularly useful for suturing during endoscopic procedures to permit tissue approximation with controlled tension.

SUMMARY OF THE INVENTION

Accordingly, it is a primary object of the present invention to provide methods, apparatus and systems for suturing tissue during endoscopic procedures in a time efficient and precise manner.

Another object of the present invention is to form a suture stitch in tissue by inserting a needle into the tissue to pass a portion of a length of suture material through the tissue from a proximal entry point to a distal exit point, forming a loop in the length of suture material at the exit point, engaging the loop with an anchor of a size to resist passing through the tissue, withdrawing or backing out the needle through the tissue and tensioning the length of suture material to controllably approximate the tissue. Additional stitches, as required, are formed in the same manner either continuously with a single length of suture material or a plurality of lengths of suture material.

A further object of the present invention is to suture tissue during an endoscopic procedure by manipulating a suturing instrument passing through a first portal in an anatomical cavity wall to reciprocate a needle carrying a length of suture material through the tissue from an entry point to an exit point and back to the entry point to form a loop at the exit point and engaging the loop with an anchor carried by an anchor applier instrument passing through a second portal in the anatomical cavity wall whereby one or more stitches can quickly be placed in the tissue with controlled tension and tissue approximation.

The present invention has another object in that a suturing instrument has a needle formed as a component thereof or integrally therewith to facilitate needle manipulation during endoscopic suturing, a mechanism to permit adjustment of the needle orientation by movement of an elongate operating member relative to a handle of the suturing instrument, an electrical connection to allow use of the needle as a cautery and/or a lumen permitting introduction of other instruments through the suturing instrument.

An additional object of the present invention is to construct an anchor applier instrument for use in suturing during an endoscopic procedure with an anchor receiver having a tapered tip for insertion in a looped portion of a length of suture material to position the looped portion around an anchor.

Some of the advantages of the present invention over the prior art are that controlled tissue approximation can be achieved to provide a "feel" similar to suturing with knots in an expeditious manner thereby increasing the variety of surgical procedures that can be performed endoscopically without increasing the time required for suturing, and that suturing can be accomplished using conventional, available instruments or specially designed instruments of simple construction allowing the instruments to be disposable or easily sterilized for reuse.

The present invention is generally characterized in a method for suturing tissue in an anatomical cavity during an endoscopic procedure including the steps of penetrating the tissue with a needle until a portion of a length of suture material attached thereto has passed through the tissue, engaging the portion of the suture material with an anchor, backing the needle out of the tissue while the suture material is held by the anchor, tensioning the suture material, and securing the suture material in the tensioned position. The present invention is further characterized in a system for suturing tissue in accordance with the above method including a needle with a length of suture material attached thereto at a position spaced from a proximal end thereof and an applier instrument carrying a plurality of anchors. A suturing instrument for use in suturing tissue in accordance with the present invention includes a needle body held by the distal end of an elongate operating member having a length to extend through a portal established in the wall of the anatomical cavity, a handle at the proximal end of the operating member and a length of suture material attached to the needle body having an enlarged proximal end. An anchor applier instrument for use in suturing according to the present invention includes a barrel housing a plurality of anchors and having a length to extend through the portal in the anatomical cavity wall, a handle receiving the proximal end of the barrel for manipulating the anchor applier instrument and an anchor receiver positioned at the distal end of the barrel for receiving anchors ejected therefrom, the anchor receiver having a tapered tip for insertion in a looped portion of the length of suture material to position the looped portion in engagement with the anchor.

Other objects and advantages of the present invention will become apparent from the following description of the preferred embodiments taken in conjunction with the accompanying drawings.

DESCRIPTION OF THE PREFERRED EMBODIMENTS

Figure 1:
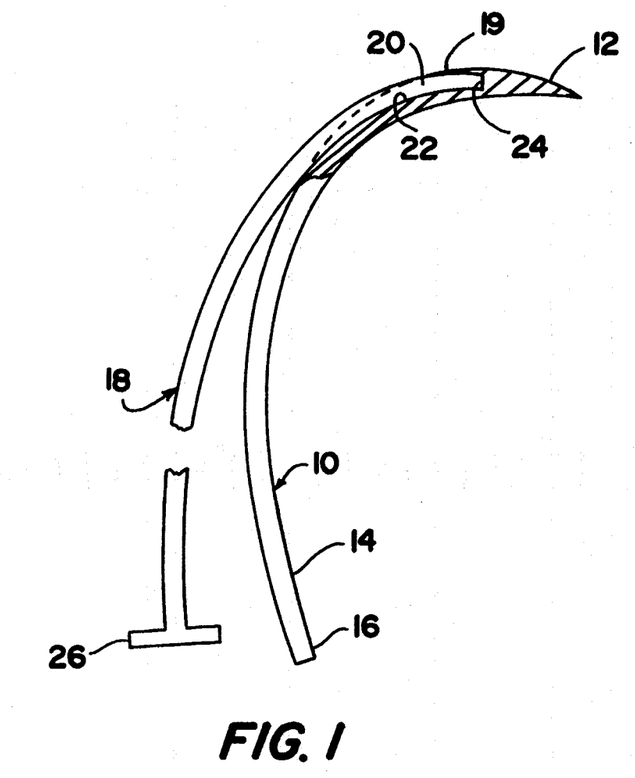
FIG. 1 is a broken side view, partly in section, of a needle with a length of suture material attached thereto for use with the present invention.

In accordance with the present invention, suturing is preferably accomplished with a suture needle 10, as shown in FIG. 1, having a sharp distal end or tip 12, a curved body 14 and a proximal end 16. A length of suture material 18 has a distal end attached to the needle body at an attachment position 19 spaced from the proximal end 16 by a distance greater than the thickness of the tissue to be sutured. In order to minimize the space required to accommodate protrusion of the needle tip beyond the exit point in the tissue, it is desirable to make the attachment position as close to the tip 12 as practical; however, as will be understood from the following, the attachment position can be anywhere along the body of the needle as long as the needle can be held at the proximal end and passed through the tissue to cause the attachment position to extend beyond the exit point to place a portion of the length of suture material at the exit point. One manner in which the suture material can be secured to the needle is to form a groove 22 in the convex side of the needle leading to a blind hole 24 and to immovably hold the distal end of the suture material in the hole by friction, adhesive, wax, fusing or the like.

Figure 3:
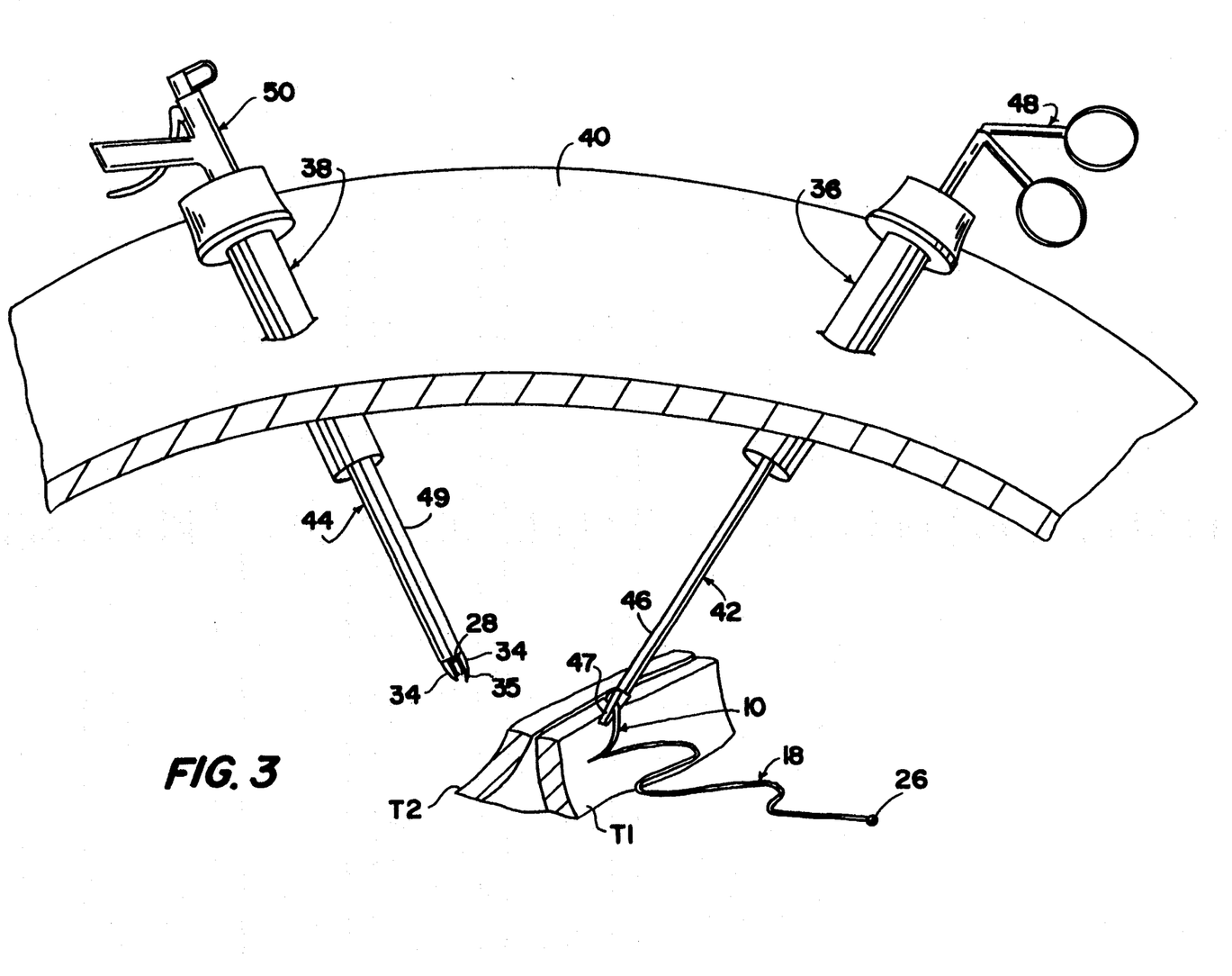
FIG. 3 is a broken perspective view, partly in section, illustrating suturing according to the present invention during an endoscopic procedure.

The suture material has a length dependent upon the procedure being performed and the number of stitches to be made, and the suture material has an enlarged proximal end 26 having a transverse dimension greater than the transverse dimension of needle 10 and suture material 18. The enlarged proximal end 26 is shown in FIG. 1 as a cross member to produce a "T" configuration and is shown in FIG. 3 as a sphere. The enlarged proximal end 26 can be formed integrally with the suture material prior to starting the suturing procedure and can have any desired configuration as well as the illustrated cross member and sphere, or the enlarged end can be formed by attaching a clip or other device to the proximal end of the suture material or by tying a knot in the suture material either during or prior to the suturing procedure. That is, the needle 10 and length of suture material 18 can be supplied to the surgeon with the enlarged proximal end 26 already in place or the enlarged proximal end can be formed by the surgeon as part of the suturing procedure. The needle 10 can have various shapes preferred for performing specific procedures and suturing particular tissue structures located at various positions within an internal body cavity, such as curved, straight, hooked or the like.

Figure 2:
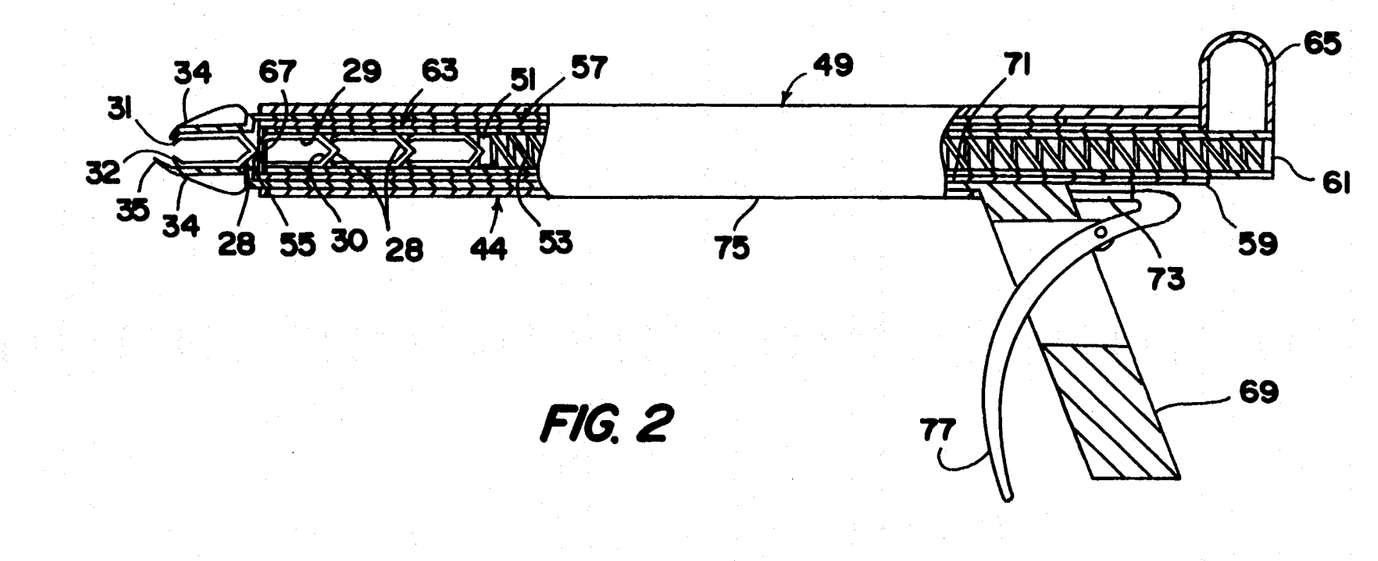
FIG. 2 is a broken side view, partly in section, of an anchor applier instrument for use with the present invention.

An anchor 28 is used to engage or capture the length of suture material once the tip 12 of the needle has passed through the tissue to be sutured. The anchor can have various configurations allowing the anchor to engage or to grip the suture material including conventional clips or staples, such as those marketed by various companies, including Ethicon Endo-Surgery, United States Surgical Company, and Linvatec Weck Endoscopy, for use in endoscopic procedures to close or occlude tissue structures. The anchor 28 is shown in FIG. 2 as a clip formed of a bent, U-shaped member of any suitable, medical grade material to have a pair of spaced, opposed legs 29 and 30 terminating at spaced distal ends 31 and 32, respectively, defining an opening therebetween. Such clips are conventionally applied to tissue with the use of a forceps-type instrument having opposing jaws 34 cooperating with the legs 29 and 30 to laterally compress or clamp the legs together; however, an instrument having a stationary jaw and a distally movable jaw to longitudinally compress or clamp the legs together, such as that shown in U.S. Pat. No. 5,171,250 to Yoon, the disclosure of which is hereby incorporated herein by reference, can also be used. While conventional clip applier instruments can be used in accordance with the present invention, it is preferred to modify such instruments such that one of the jaws is longer than and curves toward the other jaw to taper to a tip 35 that can be used to hook or hold the loop of suture material as will be appreciated from the following.

An anchor applier instrument 44, as shown in FIG. 2, includes an elongate barrel 49 extending from an open distal end adjacent jaws 34 to a proximal end received by a handle 50. A plurality of anchors 28 are housed in barrel 49 in end-to-end arrangement and are biased distally by a piston 51 and a compression spring 53 such that the inwardly turned distal ends 31 and 32 of the end anchor are held by a pair of opposing gates 55 extending radially inwardly from the distal end of a substantially cylindrical cartridge 57 having a proximal end 59 connected with a proximal end 61 of an actuator tube 63 via a U-shaped, spring handle 65. The actuator tube 63 has an open distal end 67 adjacent gates 55 such that squeezing spring handle 65 causes the actuator tube distal end 67 to open gates 55 to permit spring 53 and piston 51 to eject an anchor 28 from the barrel into the anchor receiver formed by jaws 34. Handle 50 is formed of a grip member 69 secured to a tubular, receiver support member 71 mounting jaws 34 at the distal end thereof, and grip member 69 passes through a slot 73 in an outer barrel member 75. A grip member 77 is pivotally mounted to grip member 69 and has an end coupled with the proximal end of outer barrel member 75 such that squeezing of grip members 69 and 77 moves outer barrel member 75 distally over cams 79 carried by jaws 34 to close the jaws and compress the anchor legs 29 and 30. Partial squeezing of the handle grip members 69 and 77 will cause the anchor distal ends 31 and 32 to engage; and, thereafter, the legs can be completely compressed by further squeezing of the handle grip members.

FIG. 3 illustrates suturing according to the present invention performed during an endoscopic procedure wherein portal sleeves 36 and 38 are introduced through an anatomical cavity wall 40 with the use of penetrating members such as trocars, not shown. A suturing instrument 42 is introduced into the cavity through portal sleeve 36, and the anchor applier instrument 44 is introduced into the cavity through portal sleeve 38. The suturing instrument 42 includes needle 10 with suture material 18 attached thereto and an elongate operating member 46 carrying movable jaws 47 at a distal end thereof for holding the proximal end of the needle 10. The operating member has a length to extend through portal sleeve 36 to a proximal end received by a handle 48. Numerous needle holders, sometimes also referred to as needle drivers or needle graspers, are presently available for use in endoscopic surgery and can be combined with suture needle 10 and suture material 18 to form a suturing instrument 42 according to the present invention, such needle holders being operable at proximal ends externally of the cavity by various handle mechanisms, the handle 48 being formed by pivotal grips. As discussed above, the anchor applier instrument 44 has an elongate barrel 49 housing a plurality of anchors 28 with a distal end for ejecting anchors into an anchor receiver formed by jaws 34, and the barrel has a length to extend through portal sleeve 38 to a proximal end received by a handle 50. As previously noted, numerous clip applier instruments for endoscopic procedures are available on the market and can be used as an anchor applier instrument for suturing in accordance with the present invention, preferably modified to have tapered, inwardly curving tip 35.

Figures 4, 5, 6, 7:
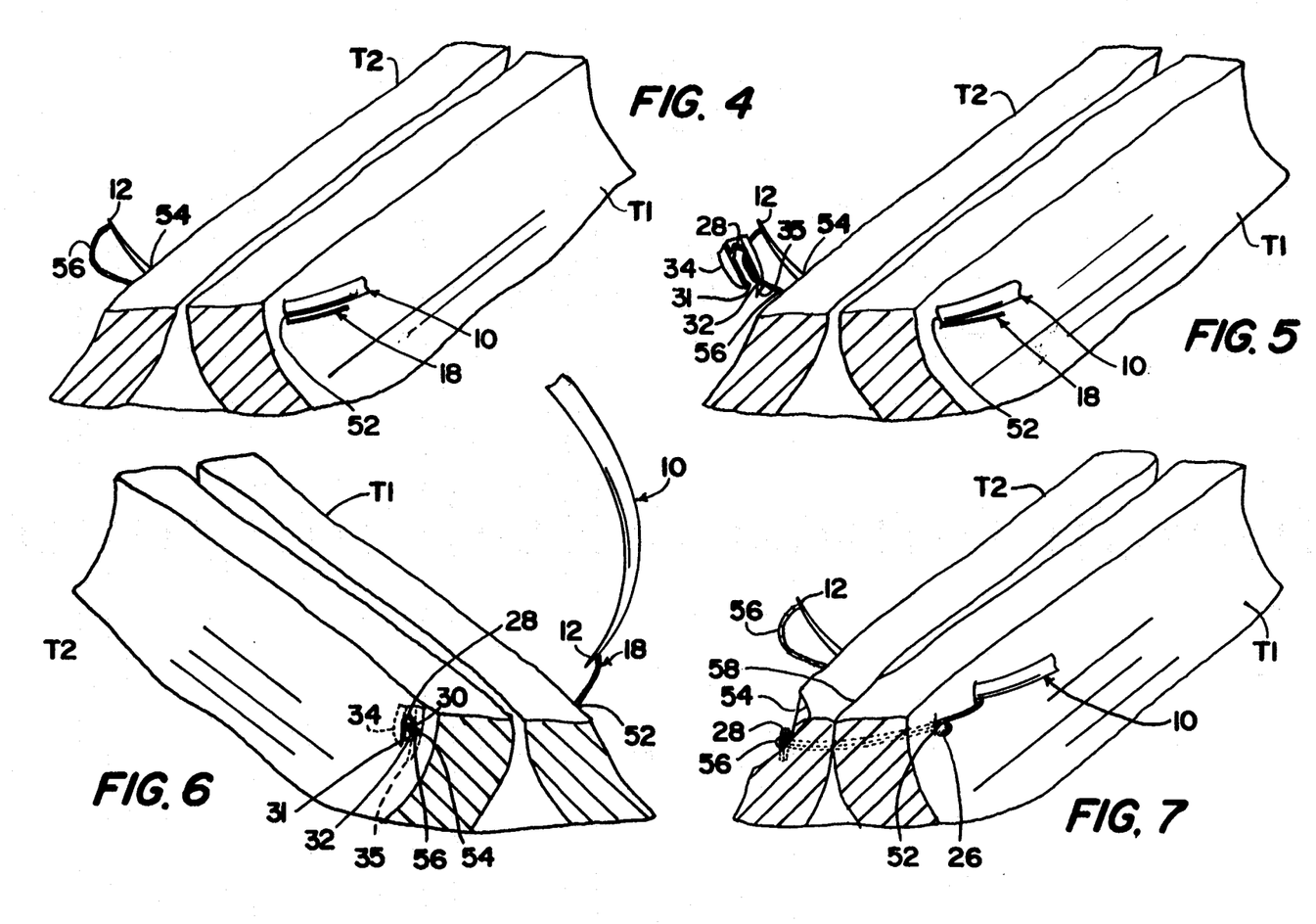
FIGS. 4, 5, 7 and 8 are broken perspective views showing suturing steps according to the present invention looking at the needle entry side of the tissue to be sutured.
FIGS. 6 and 9 are broken perspective views showing suturing steps according to the present invention looking at the needle exit side of the tissue to be sutured.

To suture tissue portions T1 and T2, suturing instrument 44 is manipulated to drive needle tip 12 through an entry point 52 in tissue portion T1 and then through tissue portion T2 and out of an exit point 54 carrying the suture material 18 through the tissue portions along with and adjacent the needle body 14 as shown in FIG.

4. When tip 12 and attachment position 19 have passed through tissue portion T2, a portion 56 of the length of suture material 18 is exposed and will bulge outwardly away from the needle to form a loop spaced from the needle body when the needle is backed out or moved proximally slightly. The anchor applier instrument is now moved to insert tapered tip 35 in the looped portion 56 and place an anchor 28 within the loop as shown in FIG. 5 to engage the suture material. When the anchor is a clip, the distal ends 31 and 32 of the clip can be clamped together while leaving the clip legs 29 and 30 spaced as shown in FIG. 6 to allow the length of suture material to move through the clip or the loop can be held by leaving the applier jaw 34 and clip within the loop 56 such that the suture material can be moved therethrough.

Figures 8, 9, 10:
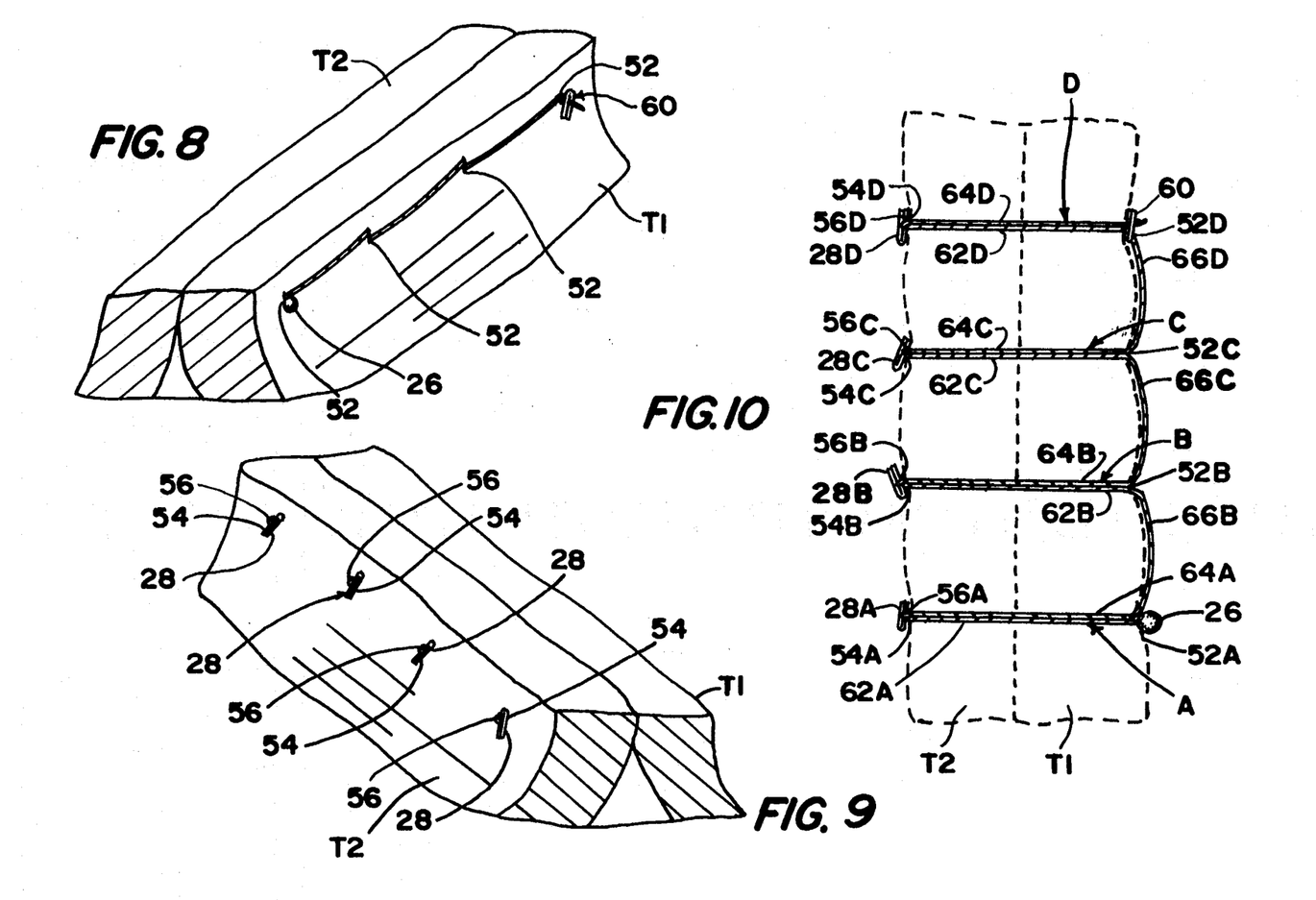
FIG. 10 is a plan view showing the arrangement of the length of suture material and anchors shown in FIGS. 8 and 9.

After the anchor and/or applier jaw has been positioned in the loop 56, the needle is backed out or withdrawn through the same opening or passage through the tissue portions pulling the suture material with it until the enlarged proximal end 26 of the suture material abuts the entry point 52 in the tissue as shown in FIG. 7. Once the enlarged end 26 of the length of suture material has been drawn up against tissue portion T1 at entry point 52, tension can be applied to the suture material by pulling the suture material around the anchor 28 and/or applier jaw to adjustably approximate tissue portions T1 and T2 as shown at 58 in FIG. 7; and, thereafter, the anchor 28 can be compressed to clamp legs 29 and 30 together to grasp the loop 56 tightly and secure the suture material in the tensioned position to complete the first stitch. If only a single stitch is required, the suture material can be cut adjacent the entry point. Of course, the stitch can also be completed by securing another anchor 28 to the length of suture material at the entry point 52 while leaving the anchor 28 at the exit point open to allow the length of suture material to slidably engage the anchor. If desired, the stitch can be completed by holding the loop with a hook and, after tensioning around the hook, applying an anchor to the loop 56 of suture material.

Where more than one stitch is required, the needle tip 12 is inserted through the tissue portions at a position spaced from the first stitch, and an anchor 28 is placed in engagement with the loop 54 formed in the second stitch in the same manner as described above with respect to the first stitch. The needle is then backed out through the same opening, and the length of suture material is tensioned to controllably approximate the tissue portions as previously described. Once one or more stitches are placed in the tissue, as required, the length of suture material is severed from the needle, and a distal anchor 60 can be secured to the distal end of the length of suture material to abut the tissue at the entry point of the last stitch, if desired, after the appropriate tension has been placed on the length of suture material to approximate the tissue as shown in FIGS. 8 and 9. An entry point anchor can be compressed or clamped to the length of suture material either after each stitch or after all stitches are completed. The entry point anchors, such as anchor 60, can have the same configuration as anchors 28 or can merely have an enlarged shape to prevent pulling of the length of suture material through the entry points.

The arrangement of the length of suture material and anchors where a plurality of stitches are made with a continuous length of suture material, as shown in FIGS. 8 and 9, is illustrated in FIG. 10 wherein the first stitch A is formed from a run 62A of the suture material extending between enlarged proximal end 26 at entry point 52A and a portion 56A engaged by and looped around anchor 28A at exit point 54A and a run 64A of the suture material extending between portion 56A and the entry point 52A adjacent run 62A. From run 64A, the length of suture material extends to the second stitch B via a connecting run 66B, and stitch B is formed from run 62B, portion 56B engaged by anchor 28B and run 64B between entry point 52B, exit point 54B and back to entry point 52B. The third stitch C and the fourth or end stitch D are similarly formed and parts thereof are given the same reference numbers with C and D added thereto, respectively. Once the suture material has been tensioned after the end stitch D, distal anchor 60 can be affixed to the end of run 64D at entry point 52D to secure the loose end of the suture material in the tensioned position, and any remaining suture material is severed and removed from the cavity. Of course, the suture material can also be severed just beyond anchor 28D eliminating run 64D depending upon whether anchor 28D is clamped to the suture material.

While any anchor of a size to resist passing through the tissue and capable of engaging the length of suture material can be used with the present invention, conventional ligating clips are advantageous since multiple clip applier instruments for endoscopic use are presently available from various companies, including Ethicon Endo-Surgery, Weck Linvatec Endoscopy and United States Surgical Company, as noted above. Other anchor configurations for use with the present invention are shown in U.S. Pat. No. 5,100,418 to Yoon et al, the disclosure of which is incorporated herein by reference, and previously mentioned U.S. Pat. No. 5,171,250 to Yoon, and are also shown in FIGS. 11, 12, 13 and 14.

Figures 11, 12, 13, 14:
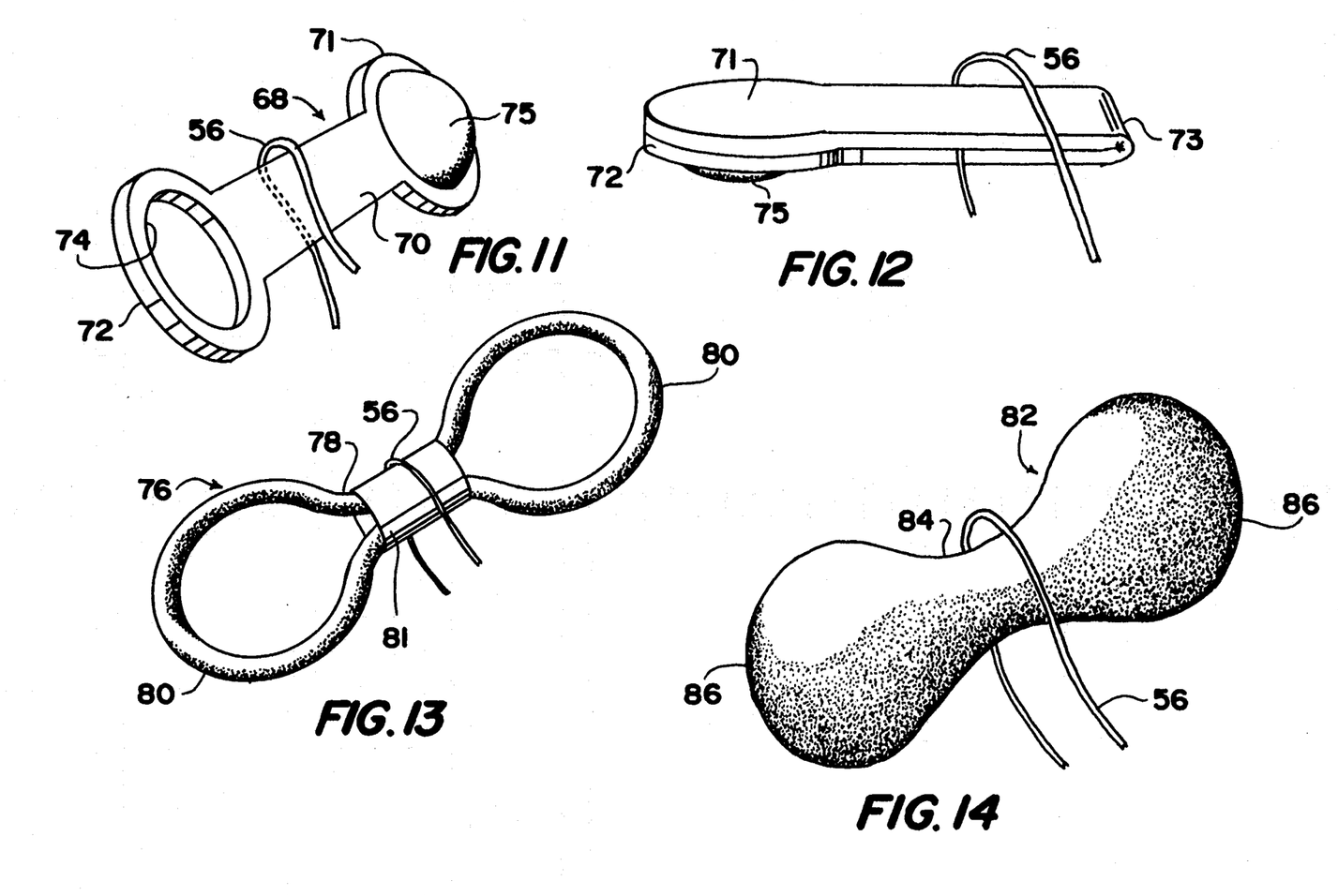
FIGS. 11, 12, 13 and 14 are perspective views of alternative anchors for use with the present invention.

In the embodiment of FIG. 11, an anchor 68 has a link or "dog bone" configuration with a smaller transverse dimension central portion 70 terminating at opposite ends at round, protruding larger transverse dimension lobes 71 and 72 such that the loop 56 of the length of suture material can be engaged by the central portion 70 with the lobes preventing the loop from slipping off of the anchor 68. The flat sides of the anchor 68 allow the anchor to be flush with tissue to be sutured; and, when an aperture 74 is formed in lobe 72, the length of suture material can be passed therethrough to secure either end thereof. By forming lobe 71 with a button 75 protruding therefrom of a size and configuration to be snapped into or frictionally held in aperture 74 in lobe 72, anchor 68 can be bent or folded on itself along a transverse axis 71 of central portion 70 to force button 75 into aperture 74 to lock suture material loop 56 therein as shown in FIG. 12. Anchor 68 can be made of any medical grade metal or plastic material allowing the anchor to be folded upon itself. In the embodiment of FIG. 13, an anchor 76 is made of a member having a circular cross-section formed in a "figure 8" configuration to have a smaller transverse dimension central portion 78 held in place by a sleeve 81, the central portion terminating at larger transverse dimension lobes 80 at opposite ends such that, similar to anchor 68, the loop 56 of the length of suture material will be engaged by the central portion 78 and captured by lobes 80. In the embodiment of FIG. 14, an anchor 82 has a barbell-like configuration with a central portion 84 and extending ends 86 to capture the loop 56 of the length of suture material in the same manner as anchors 68 and 76. When non-clamping anchors, such as 68, 76 and 82, are used to engage the loops 56 of the suture material at the exit points, it will be appreciated that the distal end of the suture material after the last stitch will be held with an anchor of the type that can be clamped or otherwise secured to the end of the suture material, such as a clip. Accordingly, the non-clamping anchors are used in the same manner as anchors 28 along with a distal anchor 60 as described above.

Figure 15:
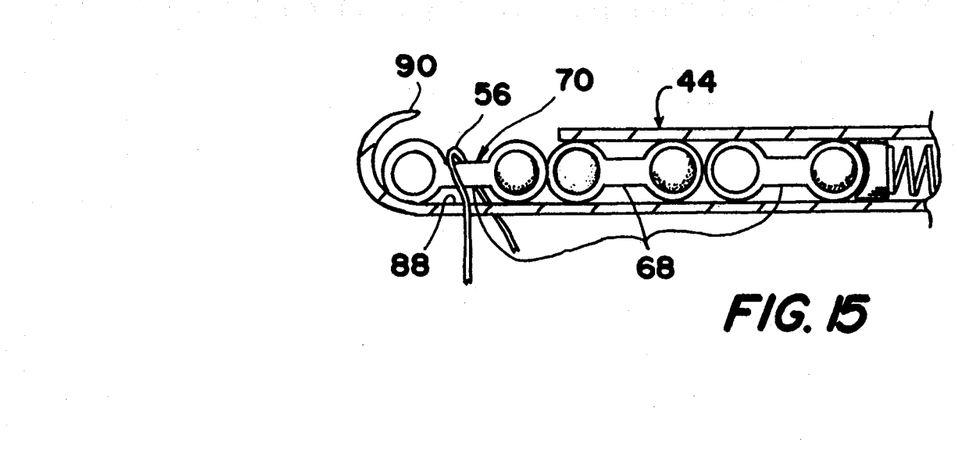
FIG. 15 is a broken side view in section of an alternative distal end of an applier instrument for the anchors of FIG. 11.

In order to facilitate engagement of the loop 56 of suture material with anchors 68, 76 or 82, the anchor applier instrument 44 can have an anchor receiving cradle 88 formed at the distal end of barrel 49 to receive anchors ejected from the barrel, the cradle terminating at a distal jaw forming a curved hook or tapered tip 90 as shown in FIG. 15, such that the tip can be inserted easily within the loop 56 to properly position an anchor within the loop. In FIG. 15, a plurality of anchors 68 are shown in end-to-end alignment in the applier; and, with an anchor 68 positioned in the cradle 88, once the distal end of the applier has been inserted in the loop, the anchor will be positioned such that the central portion 70 engages the loop 56 when the loop is tightened allowing the applier to release the anchor while the anchor is held against the tissue. Whether using lateral clamping, longitudinal clamping or cradle receivers for anchors in the anchor applier instruments, it is desirable to allow selective placement of an anchor in the receiver at the distal end of the barrel to permit use of the tip and/or jaws for other functions with no anchor in the receiver.

Figure 16:
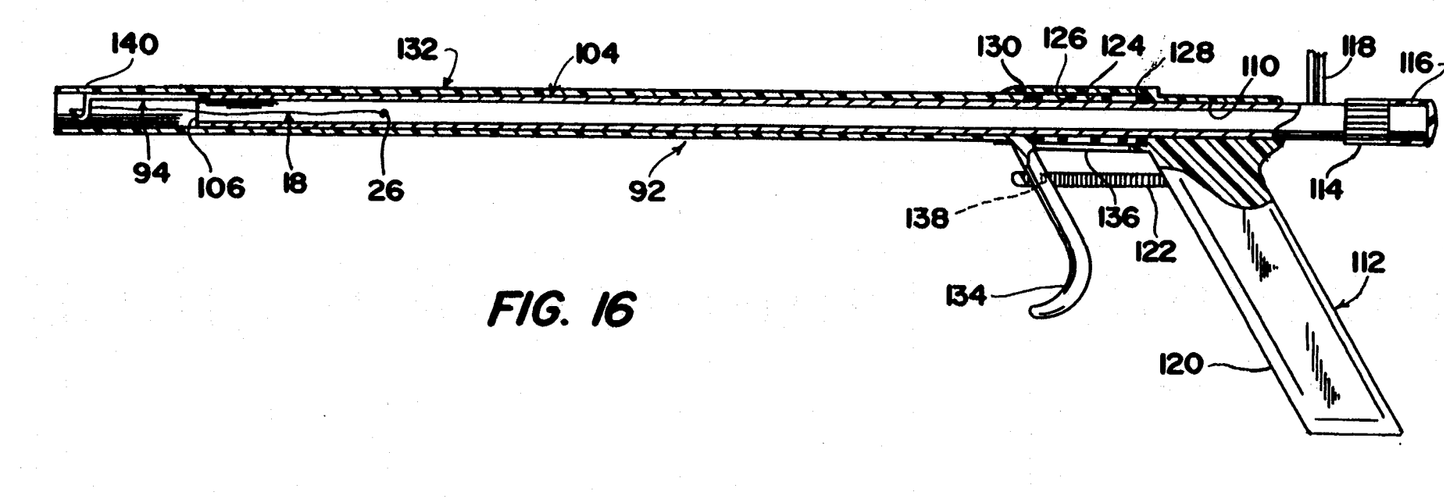
FIG. 16 is a side view, partly in section, of a suturing instrument for use with the present invention in a protective position.
Figure 17:
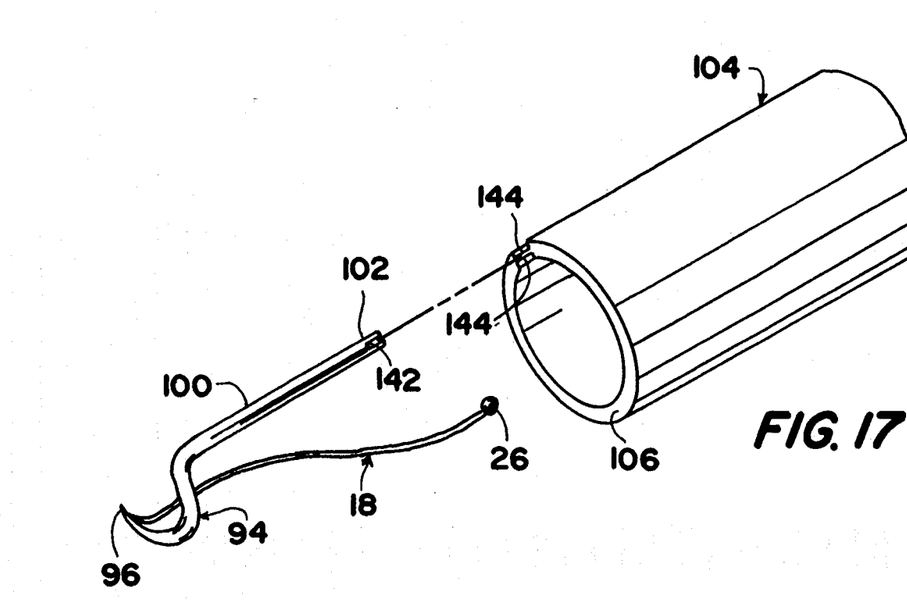
FIG. 17 is a broken, exploded, perspective view, of the distal end of the suturing instrument of FIG. 16.
Figure 18:
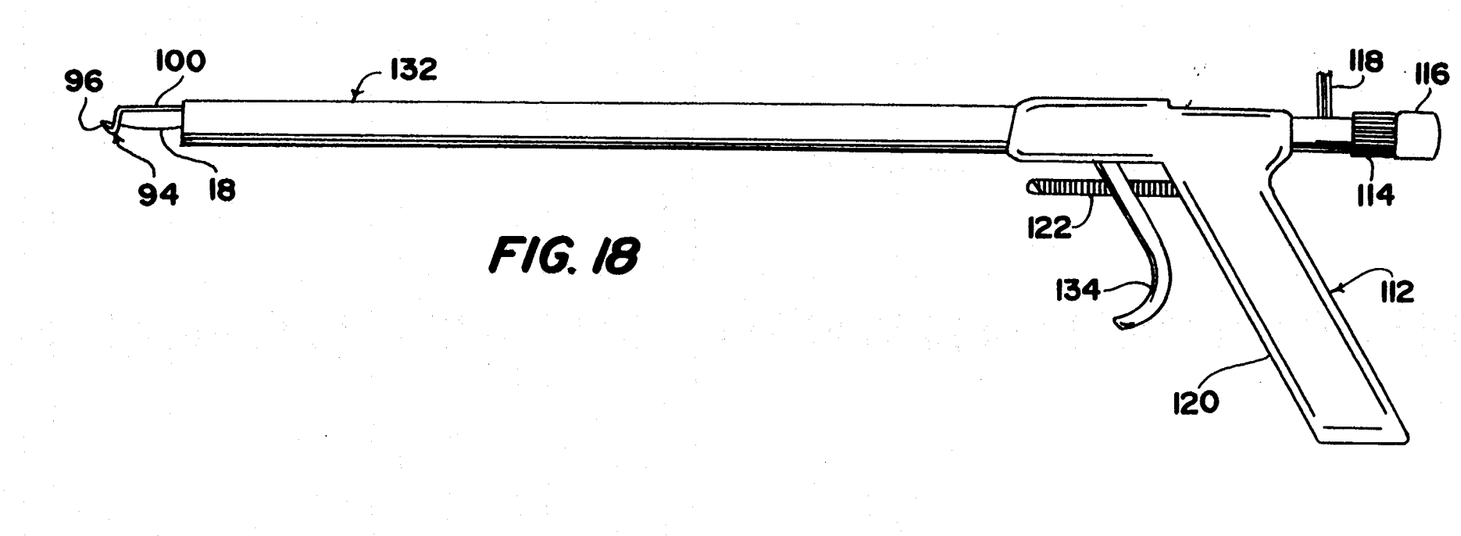
FIG. 18 is a side view of the suturing instrument of FIG. 16 in an operative position.

Another instrument 92 for suturing according to the present invention is shown in FIGS. 16, 17 and 18, the suturing instrument 92 including a needle body 94 having a sharp tip 96 at a distal end, a curved portion 98 and a shank 100 terminating at a proximal end 102, as best shown in FIG. 17. An elongate, tubular operating member 104 has a distal end 106 holding the needle body proximal end 102, a proximal end 108 rotatably, frictionally received in a bore 110 of handle 112 and a length to extend through a portal in an anatomical cavity wall. The operating member proximal end 108 carries a knurled collar 11 to facilitate rotation of the operating member relative to the handle, a plastic end cap 116 sealing the open end thereof and an electrical connector 118 extending radially therefrom. The handle 112 includes a hand grip 120, a toothed rack 122 extending distally from the hand grip and a counterbore 124 receiving a coiled spring 126 mounted in compression between a radial shoulder 128 and a proximal end 130 of a hollow, cylindrical safety shield 132 longitudinally movable in the counterbore 124 of the handle. A trigger 134 depends from the safety shield proximal end 130 through a slot 136 in the counterbore 124 and carries a pawl 138 cooperating with rack 122. Safety shield 132 has a length such that, in a distally extended protective position, a distal end 140 of the safety shield covers the needle body 94 as shown in FIG. 16 and, in a proximally retracted operative position, the needle body 94 is exposed for suturing as shown in FIG. 18.

The length of suture material 18 is attached at its distal end to needle body 94 adjacent distal tip 96 in the manner shown in FIG. 1, and enlarged proximal end 26 is disposed in the lumen of operating member 104 during insertion of the suturing instrument 92 through a portal. Needle body 94 can be formed integrally, nondetachably with the operating member 104 or can be detachably held by the operating member distal end 106, for example by forming a slot 142 in the needle body proximal end 102 to receive the peripheral edge of operating member distal end 106. Preferably, the opposing arms formed by slot 142 are received in corresponding recesses 144 in the operating member distal end to produce a smooth profile and to assure that rotation of the operating member in the handle 112 causes movement of the needle body.

In use, the suturing instrument 92 is inserted through a portal in an anatomical cavity wall with the safety shield in the protective position shown in FIG. 16 to cover the needle body 94 and prevent contact of the sharp tip with components of the portal sleeve or tissue within the cavity. Once the suturing instrument 92 has been introduced to the surgical site in the cavity, trigger 134 is squeezed to move the safety shield proximally against the bias of spring 126 to the operative position shown in FIG. 18 with the safety shield locked in place by engagement of pawl 138 with rack 122. Suturing is accomplished in the same manner as described above, and rotation of operating member 104 positions needle body 94 to facilitate manipulation for tissue penetration. If cauterization is needed during the procedure, an electrical source can be coupled to connector 118 to allow use of the needle as a unipolar cautery. To this end, operating member 104 and needle body 94 are preferably made of electrically conductive materials, such as metal; and, handle 112, end cap 116 and safety shield 132 are preferably made of electrically insulating materials, such as plastic. By removing cap 116, the lumen of operating member 104 provides communication with the anatomical cavity without removing the suturing instrument from the portal, for example to permit introduction of other instruments to the surgical site.

Figure 19:
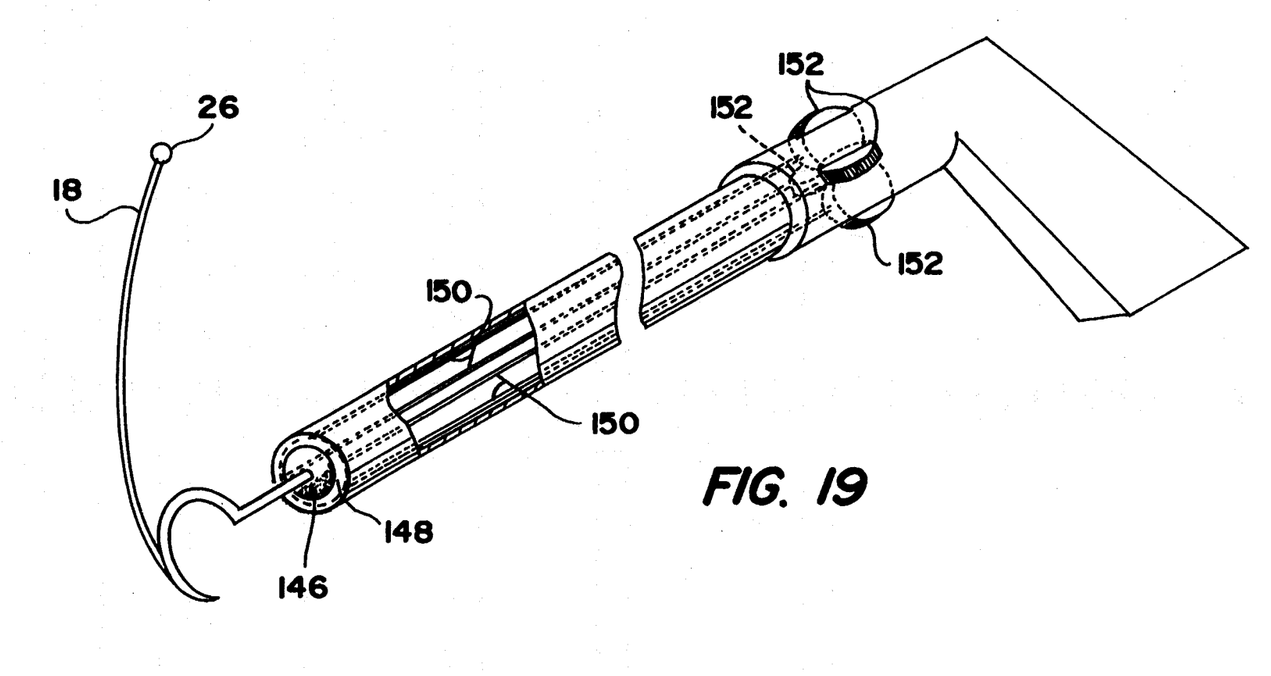
FIGS. 19 and 20 are broken perspective views of suturing instrument modifications for use with the present invention.
Figure 20:
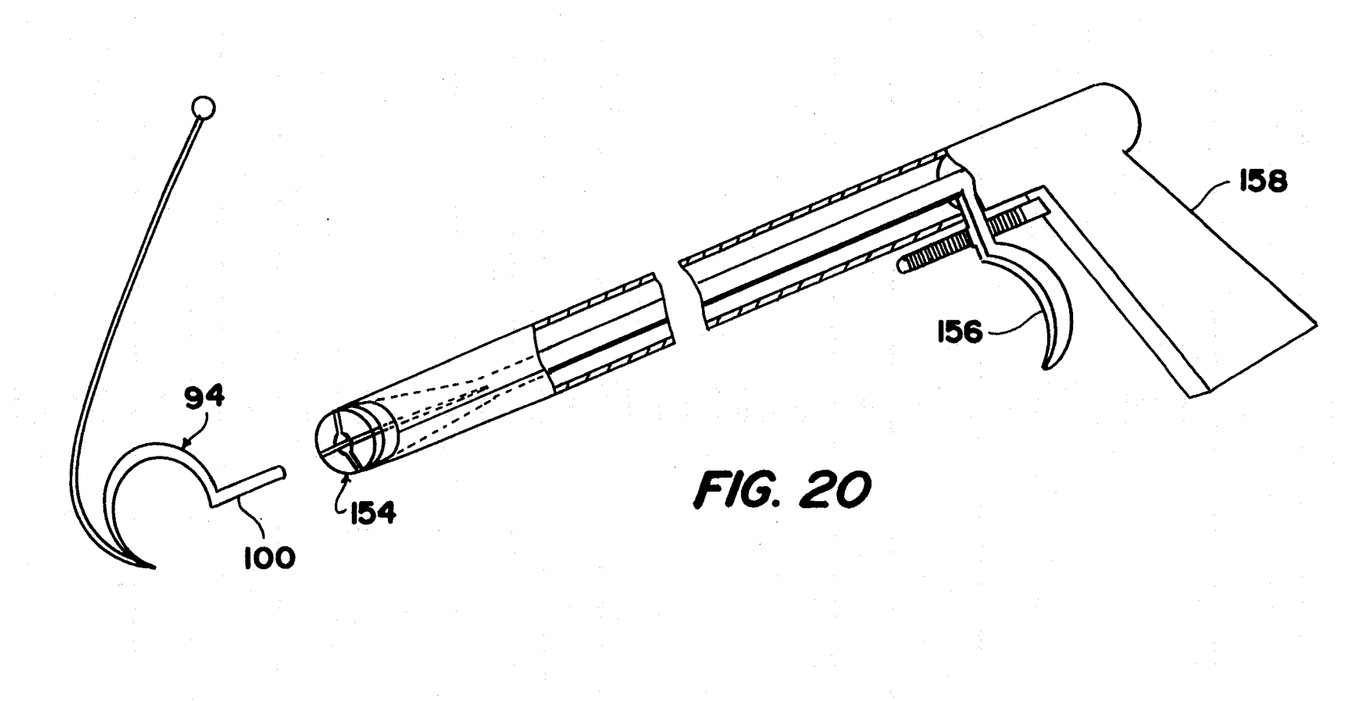

A modification of the suturing instrument is shown in FIG. 19 wherein the shank 100 of needle body 94 carries a ball 146 at the proximal end thereof movably held in a socket 148 in the distal end of the operating member, and the rotational position of the ball 146 in the socket 148 is controlled by four, equally spaced, control members 150, such as strings or wires, passing through the operating member to the handle such that longitudinal movement of the control members positions the needle body for proper suturing orientation. Each control member is connected to a wheel 152 mounted on the handle to allow positioning of the needle body by rotating the wheels with a finger. Another modification of the suturing instrument is shown in FIG. 20 wherein the shank 100 of the needle body 94 is received in a chuck 154 having four opposing jaws at the distal end of the operating member such that the shank is aligned with the longitudinal axis of the operating member for rotation therewith. The chuck is operated by a trigger 156 adjacent a handle 158 at the proximal end of the operating member. The modifications of FIGS. 19 and 20 are also preferably provided with safety shields and electrical connectors as in suturing instrument 92.

In view of the above, it will be appreciated that the present invention permits fast and precise suturing in endoscopic procedures with adjustable tension and tissue approximation. In particular, a single surgeon can quickly suture tissue by himself by manipulating a suturing instrument in one hand and an anchor applying instrument in the other hand.

Inasmuch as the present invention is subject to many variations, modifications and changes in detail, it is intended that all subject matter discussed above or shown in the accompanying drawings be interpreted as illustrative only and not be taken in a limiting sense.

What I claim is:

1. A method for suturing tissue in an anatomical cavity during an endoscopic procedure comprising the steps of
   penetrating the tissue at an entry point with a needle having a length of suture material attached thereto until a portion of the length of suture material has passed through the tissue and out of an exit point;
   providing an anchor unconnected with the length of suture material;
   engaging the portion of the length of suture material adjacent the exit point with the anchor;
   backing the needle proximally out of the tissue at the entry point while the anchor holds a portion of the length of suture material at the exit point;
   tensioning the length of suture material by pulling the length of suture material away from the entry point; and
   securing the length of suture material in the tensioned position with the anchor in contact with the tissue adjacent the exit point.

2. A method for suturing tissue as recited in claim 1 wherein said securing step includes clamping the anchor to the portion of the length of suture material at the exit point.

3. A method for suturing tissue as recited in claim 1 wherein said securing step includes clamping another anchor to the portion of the length of suture material at the entry point.

4. A method for suturing tissue as recited in claim 1 wherein the length of suture material has an enlarged proximal end and said tensioning step includes pulling the length of suture material away from the entry point to cause the enlarged proximal end to abut the tissue at the entry point.

5. A method for suturing tissue as recited in claim 1 wherein said penetrating, providing, engaging, backing out and tensioning steps form a single stitch and further comprising repeating said penetrating, providing, engaging, backing out and tensioning steps in sequence to form a plurality of stitches and thereafter performing said securing step.

6. A method for suturing tissue as recited in claim 5 wherein said securing step includes clamping another anchor to the portion of the length of suture material at the entry point for the last stitch.

7. A method for suturing tissue as recited in claim 1 wherein said penetrating, providing, engaging, backing out, tensioning and securing steps form a single stitch and further comprising repeating said penetrating, providing, engaging, backing out, tensioning and securing steps in sequence to form a plurality stitches.

8. A method for suturing tissue as recited in claim 7 wherein said securing steps include clamping the anchor for each stitch to the portion of the length of suture material at the exit point for each stitch.

9. A method for suturing tissue as recited in claim 1 and further comprising, after said penetrating step and before said engaging step, the step of proximally moving the needle a short distance to cause the portion of the length of suture material adjacent the exit point to move away from the needle to create a space therebetween.

10. A method for suturing tissue as recited in claim 9 wherein said engaging step includes positioning the anchor in the space between the portion of the length of suture material and the needle.

11. A method for suturing tissue as recited in claim 10 wherein the needle has a sharp tip and the length of suture material is attached to the needle adjacent the sharp tip and wherein said proximally moving step includes moving the sharp tip proximally toward the exit point.

12. A method for suturing tissue as recited in claim 9 wherein said engaging step includes positioning an anchor having a pair of spaced legs terminating at spaced distal ends such that the legs extend on opposite sides of the portion of the length of suture material spaced from the needle.

13. A method for suturing tissue as recited in claim 11 wherein said engaging step includes squeezing the legs of the anchor to cause the distal ends of the legs to be closed.

14. A method for suturing tissue as recited in claim 13 wherein said securing step includes squeezing the legs of the anchor to clamp the anchor to the portion of the length of suture material at the exit point.

15. A method for suturing tissue as recited in claim 1 and further comprising the step of hooking the portion of the length of suture material at the exit point prior to said engaging step.

16. A method for suturing tissue as recited in claim 1 further comprising the step of forming first and second spaced portals in a wall of the anatomical cavity and wherein said penetrating, backing out and tensioning steps are performed by a suturing instrument passing through the first portal and manipulated via a handle disposed externally of the anatomical cavity and said providing and engaging steps are performed by an anchor applier instrument holding a plurality of anchors passing through the second portal and manipulated via a handle disposed externally of the anatomical cavity.

17. A kit for suturing tissue in an anatomical cavity during an endoscopic procedure comprising
   a needle having a body terminating at a distal portion having a sharp distal end for penetrating the tissue to be sutured and an opposing proximal end to be held for manipulating the needle body in the cavity through a first portal in a wall of the cavity;
   a length of suture material having a distal end immovably attached to said needle body distal portal at an attachment position spaced from said needle proximal end by a distance greater than the thickness of the tissue to be sutured such that manipulation of said needle body to cause said sharp distal end to penetrate forwardly through the tissue to be sutured at an entry point and out of an exit point pulls a portion of said length of suture material out of the exit point to form a loop of the portion of said length of suture material adjacent the exit point; and
   an applier instrument carrying a plurality of anchors for application at a distal end of said applier instrument, said anchors having a configuration to engage said loop of said suture material, said applier instrument being manipulated in the cavity through a second portal through the cavity wall to place one of said anchors in engagement with said loop of said suture material to hold said loop of said suture material when said needle body is withdrawn rearwardly from the tissue and away from the entry point.

18. The system as recited in claim 17 wherein said anchors are clips having apposed legs movable to clamp said loop of said suture material.

19. The system as recited in claim 17 wherein said anchors have a central portion with opposing ends having transverse dimensions larger than the transverse dimension of said central portion, said loop of said suture material extending around said central portion of said anchors.

20. The system as recited in claim 17 wherein said applier instrument distal end includes a jaw tapering to a tip for hooking or holding said loop of said suture material.

21. The system as recited in claim 17 wherein said applier instrument distal end includes opposed jaws, one of said jaws being longer than the other of said jaws and curving toward said other jaw to taper to a tip for hooking or holding said loop of said suture material.

22. The system as recited in claim 17 and further comprising an elongate operating member holding said proximal end of said needle body and having a length to extend through the second portal.

23. A suturing instrument for use in suturing tissue in an anatomical cavity during an endoscopic procedure by inserting said suturing instrument through a portal in a wall of the anatomical cavity, said suturing instrument comprising
   a needle having a body terminating at a sharp distal end and an opposing proximal end;
   an elongate operating member having a distal end holding said needle body at said needle body proximal end and having a length to extend through the portal to a proximal end;
   a handle receiving said operating member proximal end for manipulating said needle body within the anatomical cavity; and
   a length of suture material having a distal end attached to said needle body at an attachment position spaced from said needle proximal end by a distance greater than the thickness of the tissue to be sutured such that manipulation of said needle body to cause said sharp distal end to penetrate forwardly through the tissue to be sutured at an entry point and out of an exit point pulls a portion of said length of suture material out of the exit point to form a loop of said length of suture material adjacent the exit point, said length of suture material having an enlarged proximal end having a transverse dimension greater than the transverse dimension of said length of suture material.

24. A suturing instrument as recited in claim 23 wherein said needle body proximal end is detachably held by said operating member distal end.

25. A suturing instrument as recited in claim 24 wherein said operating member distal end includes opposed relatively movable jaws for holding said needle body proximal end.

26. A suturing instrument as recited in claim 24 wherein said operating member has a longitudinal axis, said needle body proximal end includes a shank having a longitudinal axis aligned with said operating member longitudinal axis, and said needle body has a portion curving away from said shank, said shank being held by said operating member distal end whereby rotation of said operating member about said operating member longitudinal axis adjusts the position of said needle body to facilitate suturing.

27. A suturing instrument as recited in claim 23 wherein said needle body is integrally, undetachably formed with said operating member.

28. A suturing instrument as recited in claim 23 wherein said operating member has a longitudinal axis and said operating member proximal end is received in said handle to be selectively rotatable therein about said longitudinal axis.

29. A suturing instrument as recited in claim 28 wherein said needle body proximal end is held by said operating member distal end at a position spaced from said longitudinal axis.

30. A suturing instrument as recited in claim 23 wherein said operating member is tubular to form a lumen extending between said operating member proximal end distal ends providing communication with the anatomical cavity without removing said suturing instrument from the portal.

31. A suturing instrument as recited in claim 23 and further comprising an electrical connector carried on said operating member proximal end to permit use of said needle body as a cautery.

32. A suturing instrument as recited in claim 23 and further comprising a hollow safety shield movable between a distally extended protective position covering said needle body and a proximally retracted operative position exposing said needle body.

33. A suturing instrument as recited in claim 32 wherein said safety shield is mounted on said handle and includes means biasing said safety shield toward said extending protective position and a trigger for moving said safety shield to said retracted operative position against said bias means.

34. A suturing instrument as recited in claim 23 wherein said needle body proximal end is movably held by said operating member distal end and further comprising control member means extending along said operating member from said needle body proximal end to said handle for moving said needle body relative to said operating member.

35. A suturing instrument as recited in claim 34 wherein said needle body proximal end includes a ball, said operating member distal end includes a socket capturing said ball and said control member means includes a plurality of control members attached to said ball.

36. A method for suturing tissue in an anatomical cavity during an endoscopic procedure comprising the steps of
   penetrating the tissue at an entry point with a needle having a length of suture material immovably attached to a distal portion thereof until a portion of the length of suture material has passed through the tissue and out of an exit point;
   proximally moving the needle a short distance to cause the portion of the length of suture material adjacent the exit point to move away from the needle to create a space therebetween forming a loop;
   inserting an instrument in the loop formed by the portion of the length of suture material adjacent the exit point to engage the length of suture material;
   backing the needle proximally out of the tissue at the entry point while holding a portion of the length of suture material at the exit point;
   tensioning the length of suture material by pulling the length of suture material away from the entry point; and securing the length of suture material in the tensioned position.

37. A method for suturing tissue as recited in claim 36 wherein said inserting step includes grasping the loop formed by the portion of the length of suture material adjacent the exit point.

38. A method for suturing tissue as recited in claim 37 wherein said grasping step includes grasping the loop formed by the portion of the length of suture material adjacent the exit point on opposing sides of the length of suture material.

39. A method for suturing tissue as recited in claim 38 wherein said grasping step includes grasping the loop formed by the portion of the length of suture material adjacent the exit point with opposing legs of a clip.

40. A suturing instrument for use in suturing tissue comprising a needle having a solid body terminating at a distal portion having a sharp distal end and an opposing proximal end said needle body having a blind hole formed in said distal portion; and a length of suture material having a distal end immovably disposed and held in said blind hole in said needle body distal portion adjacent said sharp distal end of said needle such that manipulation of said needle body to cause said sharp distal end to penetrate forwardly through the tissue to be sutured at an entry point and out of an exit point pulls a portion of said length of suture material out of the exit point to form a loop of said length of suture material adjacent the exit point.

41. A suturing instrument for use in suturing tissue as recited in claim 40 wherein said needle body is curved and has a convex side with a groove therein leading to said blind hole.

* * * * *